(12) United States Patent
Alsalhi et al.

(10) Patent No.: US 10,780,111 B1
(45) Date of Patent: Sep. 22, 2020

(54) CALCIUM HYDROXIDE NANOPARTICLES SYNTHESIZED WITH CAROB PULP EXTRACT

(71) Applicant: KING SAUD UNIVERSITY, Riyadh (SA)

(72) Inventors: Mohamad Saleh Alsalhi, Riyadh (SA); Sandhansamy Devanesan, Riyadh (SA); Rawan Ibrahim Salem Alkhalaf, Al-Rass (SA); Hajer Saad Abdullah Allayed, Riyadh (SA); Nasser Raqe Rashed Alqhtani, Riyadh (SA); Mohammed Ghazi Alkindi, Riyadh (SA); Osama Ghurmullah Mohammed Alghamdi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/397,286

(22) Filed: Apr. 29, 2019

(51) Int. Cl.
| | |
|---|---|
| *A61K 33/08* | (2006.01) |
| *C01F 11/02* | (2006.01) |
| *B01D 11/02* | (2006.01) |
| *A61K 9/16* | (2006.01) |

(52) U.S. Cl.
CPC ............ *A61K 33/08* (2013.01); *A61K 9/1652* (2013.01); *A61K 9/1682* (2013.01); *B01D 11/0288* (2013.01); *C01F 11/02* (2013.01); *C01P 2002/01* (2013.01); *C01P 2002/72* (2013.01); *C01P 2002/76* (2013.01);
(Continued)

(58) Field of Classification Search
None
See application file for complete search history.

(56) References Cited

U.S. PATENT DOCUMENTS

| | | | |
|---|---|---|---|
| 3,297,583 A | 1/1967 | Dierichs | |
| 2010/0028471 A1* | 2/2010 | Maestro | ............. A61K 8/97 424/774 |
| 2016/0249636 A1 | 9/2016 | Ellis et al. | |

FOREIGN PATENT DOCUMENTS

WO     2013178945 A1    12/2013

OTHER PUBLICATIONS

Samanta et al. ("Synthesis of Nano Calcium Hydroxide in Aqueous Medium", J. Am. Ceram. Soc., 99 [3] 787-795 (2016) (Year: 2016).*

(Continued)

*Primary Examiner* — Aradhana Sasan
*Assistant Examiner* — Quanglong N Truong
(74) *Attorney, Agent, or Firm* — Nath, Goldberg & Meyer; Richard C. Litman

(57) ABSTRACT

Calcium hydroxide nanoparticles ($Ca(OH)_2NPs$) synthesized using carob pulp extract may be hexagonal nanoparticles with a diameter ranging from about 31.22 nm to about 81.22 nm. The $Ca(OH)_2NPs$ may be synthesized by heating ethylene glycol, adding calcium hydroxide to the ethylene glycol to provide a first mixture, heating the first mixture, adding a carob pulp aqueous extract to the first mixture to form a second mixture, heating the second mixture, adding sodium hydroxide (NaOH) to the second mixture to form a third mixture, heating the third mixture, resting the third mixture at room temperature after heating, centrifuging the third mixture, collecting a colloid sediment, extracting any unwanted contaminants from the colloid sediment, and drying the colloid sediment to obtain $Ca(OH)_2NPs$.

9 Claims, 5 Drawing Sheets

(52) U.S. Cl.
CPC ...... *C01P 2002/82* (2013.01); *C01P 2002/85* (2013.01); *C01P 2004/03* (2013.01); *C01P 2004/64* (2013.01)

(56) References Cited

OTHER PUBLICATIONS

Owen, R.W., et al., "Isolation and structure elucidation of the major individual polyphenols in carob fibre," Food Chem Toxicol. 41(12): 1727-38, 2003.

Samanta, A., et al., "Synthesis of Nano Calcium Hydroxide in Aqueous Medium," J. of the Am. Ceramic Society 2015.

Awaad, A.M. et al., "Green synthesis of silver nanoparticles using carob leaf extract and its antibacterial activity," International J. of Industrial Chem 4(29): 1-6, 2013.

Roy, A., and Bhattacharya, J., "Synthesis of Ca(OH)2 nanoparticles by wet chemical method," Micro & Nano Letters, 5(2): 131-134, 2010.

\* cited by examiner

CALCIUM HYDROXIDE NANOPARTICLES SYNTHESIZED WITH CAROB PULP EXTRACT

BACKGROUND

1. Field

The disclosure of the present patent application relates to nanotechnology, and particularly to a method of synthesizing calcium hydroxide nanoparticles using carob pulp extract.

2. Description of the Related Art

In materials science, nanomaterials have demonstrated unique size and morphology based characteristics. Nanotechnology is an emerging field demonstrating significant potential for the development of new medicines. The most common methods of producing nanoparticles are chemical or mechanical, including ball milling, thermal quenching, precipitation techniques, and vapor deposition. However, these methods are often costly, and may result in toxic byproducts.

Biological approaches for synthesizing nanoparticles can avoid many of the disadvantages associated with the chemical or mechanical synthesis methods.

Thus, calcium hydroxide nanoparticles synthesized with carob pulp extract solving the aforementioned problems are desired.

SUMMARY

Calcium hydroxide nanoparticles ($Ca(OH)_2NPs$) synthesized using carob pulp extract may be hexagonal nanoparticles with a diameter ranging from about 31.22 nm to about 81.22 nm. The $Ca(OH)_2NPs$ may be synthesized by heating ethylene glycol, adding calcium hydroxide to the ethylene glycol to provide a first mixture, heating the first mixture, adding a carob pulp aqueous extract to the first mixture to form a second mixture, heating the second mixture, adding sodium hydroxide (NaOH) to the second mixture to form a third mixture, heating the third mixture, resting the third mixture at room temperature after heating, centrifuging the third mixture, collecting a colloid sediment, extracting any unwanted contaminants from the colloid sediment, and drying the colloid sediment to obtain $Ca(OH)_2NPs$. The $Ca(OH)_2NPs$ may be useful in a wide variety of applications including but not limited to water purification, paper preservation, antimicrobial agent applications, and in treating dental diseases, including but not limited to dental abscesses.

An embodiment of the present subject matter is directed to a composition including $Ca(OH)_2NPs$ and carob pulp extract.

An embodiment of the present subject matter is directed to a pharmaceutical composition comprising the $Ca(OH)_2NPs$ and a pharmaceutically acceptable carrier.

An embodiment of the present subject matter is directed to a method of making a pharmaceutical composition including mixing the $Ca(OH)_2NPs$ with a pharmaceutically acceptable carrier.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
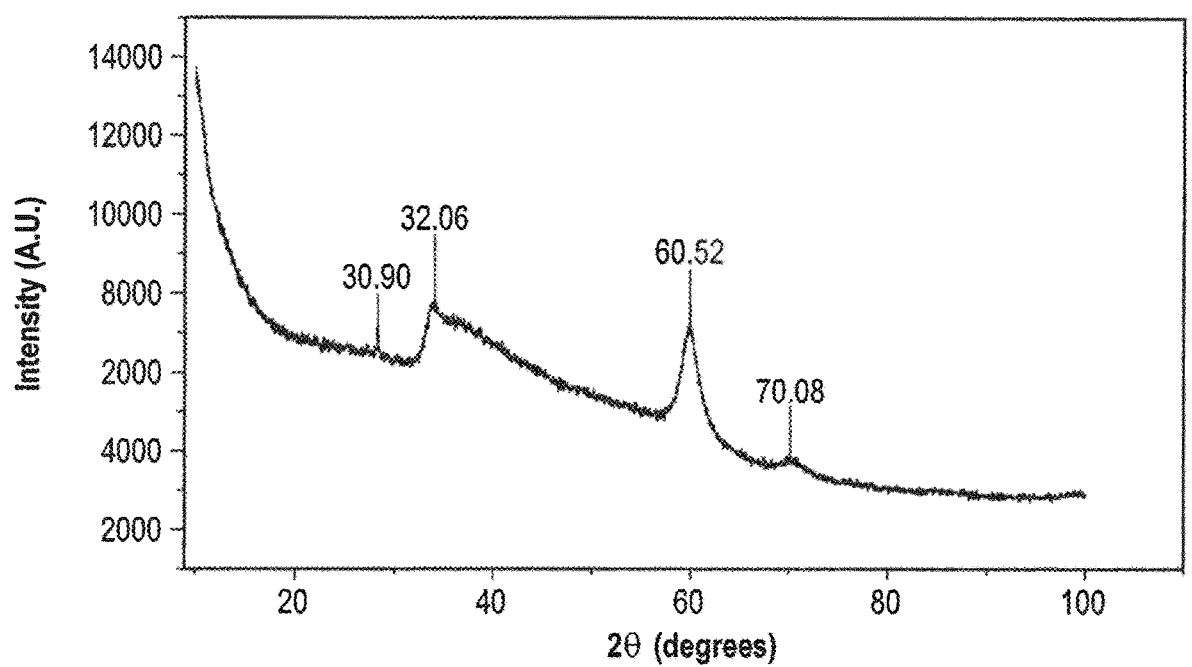
FIG. 1 depicts an X-ray diffraction spectrum of the calcium hydroxide nanoparticles synthesized with carob pulp extract.

Calcium hydroxide nanoparticles synthesized using carob pulp extract may be hexagonal nanoparticles with a diameter ranging from about 31.22 nm to about 81.22 nm. The $Ca(OH)_2NPs$ may be synthesized by heating ethylene glycol, adding calcium hydroxide to the ethylene glycol to provide a first mixture, heating the first mixture, adding a carob pulp aqueous extract to the first mixture to form a second mixture, heating the second mixture, adding sodium hydroxide (NaOH) to the second mixture to form a third mixture, heating the third mixture briefly, resting the third mixture after heating, centrifuging the third mixture at least once, collecting a colloid sediment, extracting any unwanted contaminants from the colloid sediment, and drying the colloid sediment to obtain $Ca(OH)_2NPs$. In an embodiment, unwanted contaminants can be extracted in isopropanol. The $Ca(OH)_2NPs$ may be useful in a wide variety of applications, including but not limited to, water purification, paper preservation, antimicrobial applications, and in treating dental diseases, including but not limited to dental abscesses.

In an embodiment, the heating may be performed in an ultrasonic water bath heated to a temperature of about 99.9° C. In an embodiment, the ethylene glycol is heated in an ultrasonic water bath for about 10 minutes at about 99.9° C. In an embodiment, the first mixture is heated in an ultrasonic water bath for about 15 minutes at about 99.9° C. In an embodiment, the second mixture is heated in an ultrasonic water bath for about 15 minutes at about 99.9° C. In an embodiment, the third mixture is heated in an ultrasonic water bath for about 5 minutes at about 99.9° C.

As used herein, the term "about," when used to modify a numerical value, means within ten percent of that numerical value.

In an embodiment, the carob pulp aqueous extract may be synthesized by collecting carob fruit, drying the carob fruit to provide a dried carob fruit, and reducing the dried carob fruit to a fine powder. For example, the dried carob fruit, e.g., pulp and/or seeds, can be ground to produce the carob fruit powder. The carob fruit powder can be suspended in a liquid, e.g., water. The suspension can be filtered to produce the carob pulp aqueous extract. In an embodiment, the suspension can be filtered using Whatman® No. 1 filter paper to produce the carob pulp aqueous extract.

In an embodiment, the carob fruit used to synthesize the carob pulp aqueous extract may be grown in Saudi Arabia.

In an embodiment, 1 Kg of carob fruit may be used to make the carob pulp aqueous extract.

In an embodiment, about 50 ml of ethylene glycol is heated in the ultrasonic water bath for about 10 minutes. Then, about 25 g of calcium hydroxide is added to the ethylene glycol to form the first mixture. The calcium hydroxide and ethylene glycol solution may be stirred in the ultrasonic water bath until the calcium hydroxide is completely dissolved (about 15 minutes). About 50 ml of carob pulp aqueous extract is slowly added to the first mixture in the ultrasonic water bath over a period of about 15 minutes to form the second mixture. A 1 M concentration of NaOH is then slowly added to the second mixture in the ultrasonic water bath over a period of about 5 minutes to form the third mixture. The third mixture is rested at room temperature.

In an embodiment the third mixture is centrifuged at about 15000 RPM for about 30 minutes. The supernatant is then discarded and a colloid sediment is collected. Unwanted contaminants from the colloid sediment can be removed from the colloid sediment by mixing isopropanol with the colloid sediment and centrifuging the mixture of isopropanol and colloid sediment at about 15000 RPM for about 30 minutes. The process of extracting unwanted chemical contaminants from a colloid sediment obtained from a centrifugation cycle (by mixing isopropanol with the colloid sediment and centrifuging the mixture of isopropanol and colloid sediment) can be repeated one or more times, e.g., three or four times, to extract unwanted chemical contaminants from the colloid sediment An embodiment of the present subject matter is directed to a composition including $Ca(OH)_2NPs$ and carob pulp extract.

An embodiment of the present subject matter is directed to a pharmaceutical composition comprising the $Ca(OH)_2NPs$ and a pharmaceutically acceptable carrier.

An embodiment of the present subject matter is directed to a method of making a pharmaceutical composition including mixing the $Ca(OH)_2NPs$ with a pharmaceutically acceptable carrier. For example, the method of making a pharmaceutical composition can include mixing the $Ca(OH)_2NPs$ under sterile conditions with a pharmaceutically acceptable carrier with preservatives, buffers, and/or propellants to create the pharmaceutical composition.

An embodiment of the present subject matter is directed to a pharmaceutical composition including the $Ca(OH)_2NPs$. To prepare the pharmaceutical composition, the $Ca(OH)_2NPs$, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms, such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose.

The following examples illustrate the present teachings.

Example 1

Synthesis of Calcium Hydroxide Nanoparticles with Carb Pulp Extract

Carob pulp aqueous extract was produced by washing carob fruits with tap water and deionized water, drying the fruit under laboratory conditions, grinding the dried fruit to a fine powder, soaking the powder in water, and filtering extract with Whatman No. 1 filter paper. Calcium hydroxide nanoparticles were synthesized with the Carob pulp extract as follows. Ethylene glycol (about 50 ml) was placed in a conical flask in an ultrasonic water bath for ten minutes at the maximum temperature of 99.9° C. About 25 g of calcium hydroxide was added to the ethylene glycol solution under constant stirring until the calcium hydroxide completely dissolved (about 15 minutes). The resulting first mixture appeared as a thick suspension. The Carob pulp aqueous extract (about 50 ml) was slowly added to the first mixture under constant stirring at a maximum temperature of 99.9° C. over a period of about 15 minutes, producing a second mixture. Sodium hydroxide (1 M) was then slowly added to the second mixture at the maximum temperature of 99.9° C. over about 5 minutes, and the resulting third mixture was allowed to rest without stirring. The third mixture was then centrifuged at 15,000 RPM for about 30 minutes, the supernatant was discarded, and the colloid sediment was collected. A volume of isopropanol was added to the colloid sediment, mixed well and centrifuged at 15,000 RPM for about 15 minutes. The supernatant was discarded and the colloid sediment was collected. The process of collecting the colloid sediment after centrifuging, mixing the colloid sediment with isopropanol, and centrifuging the resulting mixture was repeated three times. The final resulting colloid sediment was then dried to form a $Ca(OH)_2NP$ powder.

Example 2

Confirmation of Calcium Hydroxide Nanoparticles Synthesis with Carb Pulp Extract $Ca(OH)_2NPs$ produced according to the method of Example 1 were analyzed as follows.

X-ray diffraction of the $Ca(OH)_2NPs$ revealed four distinct peaks at 30.90, 32.06, 60.52, and 70.08 2θ degrees, respectively (FIG. 1). These peaks confirm the presence of calcium hydroxide nanoparticles at a high degree of purity.

Figure 2:
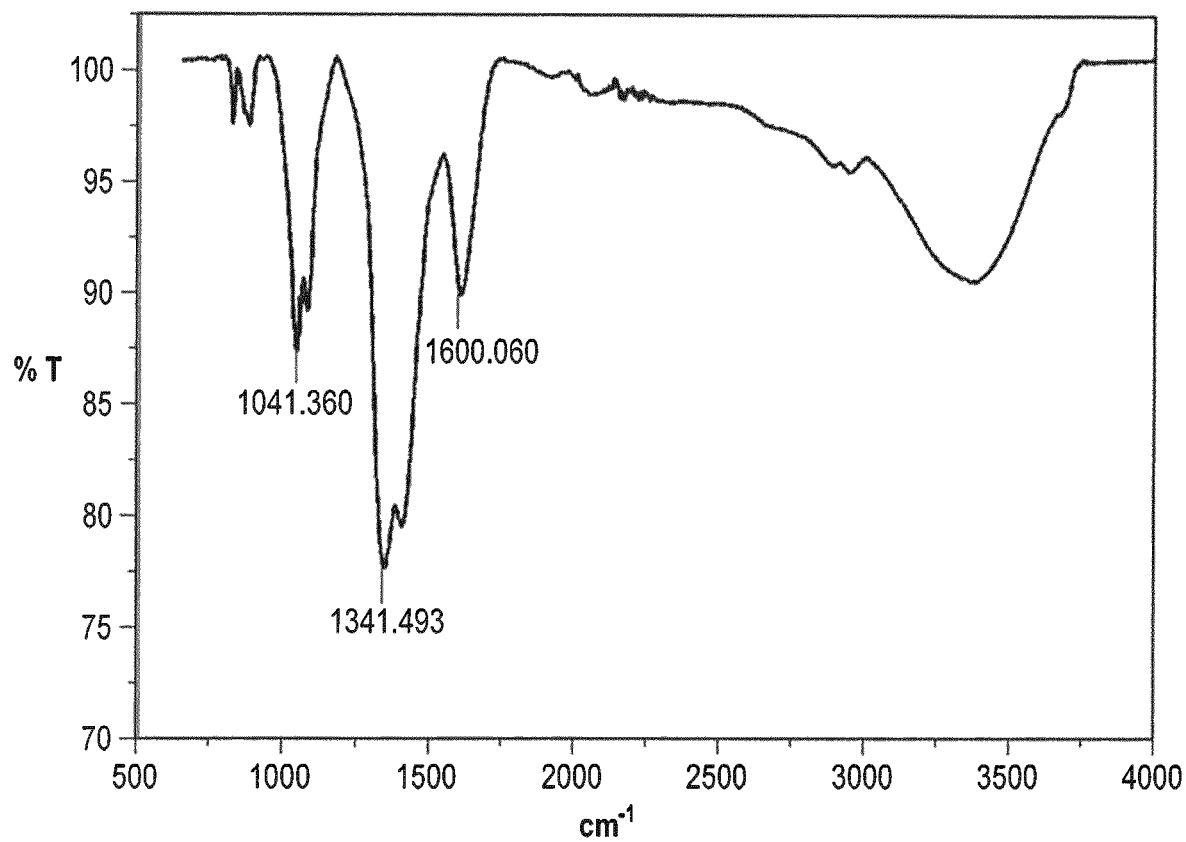
FIG. 2 depicts an attenuated total reflectance Fourier-transform infrared spectrum of the calcium hydroxide nanoparticles synthesized with carob pulp extract.

The attenuated total reflection (ATR) spectrum of the $Ca(OH)_2NPs$ confirmed the presence of functional groups, such as carbonyls, alcohols, carboxylic acids, esters, and amines in the $Ca(OH)_2NPs$ (FIG. 2). The spectrum shows three bands, including one at $1041.36\ cm^{-1}$ corresponding to a C—OH(OH) group, a stretching vibration band at $1341.49\ cm^{-1}$ corresponding to a C—C group, and a band at $1600.49\ cm^{-1}$ corresponding to a CO—NH group. These results confirm organic mediated synthesis of $Ca(OH)_2NPs$.

Figure 3:
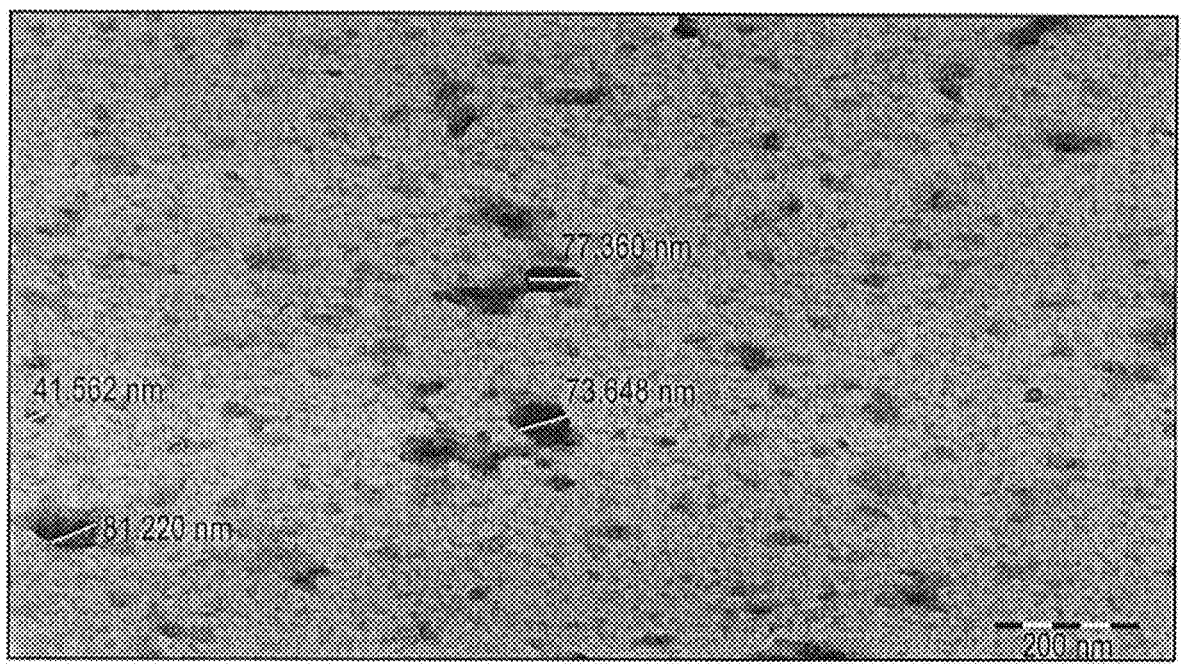
FIG. 3 depicts a transmission electron micrograph of the calcium hydroxide nanoparticles synthesized with carob pulp extract.

Transmission electron microscopy (TEM) was used to characterize the size and shape of the Ca(OH)$_2$NPs. The Ca(OH)$_2$NPs were found to be hexagonal, with a minimum diameter of about 31.22 nm and a maximum diameter of about 81.22 nm (FIG. 3).

Figure 4:
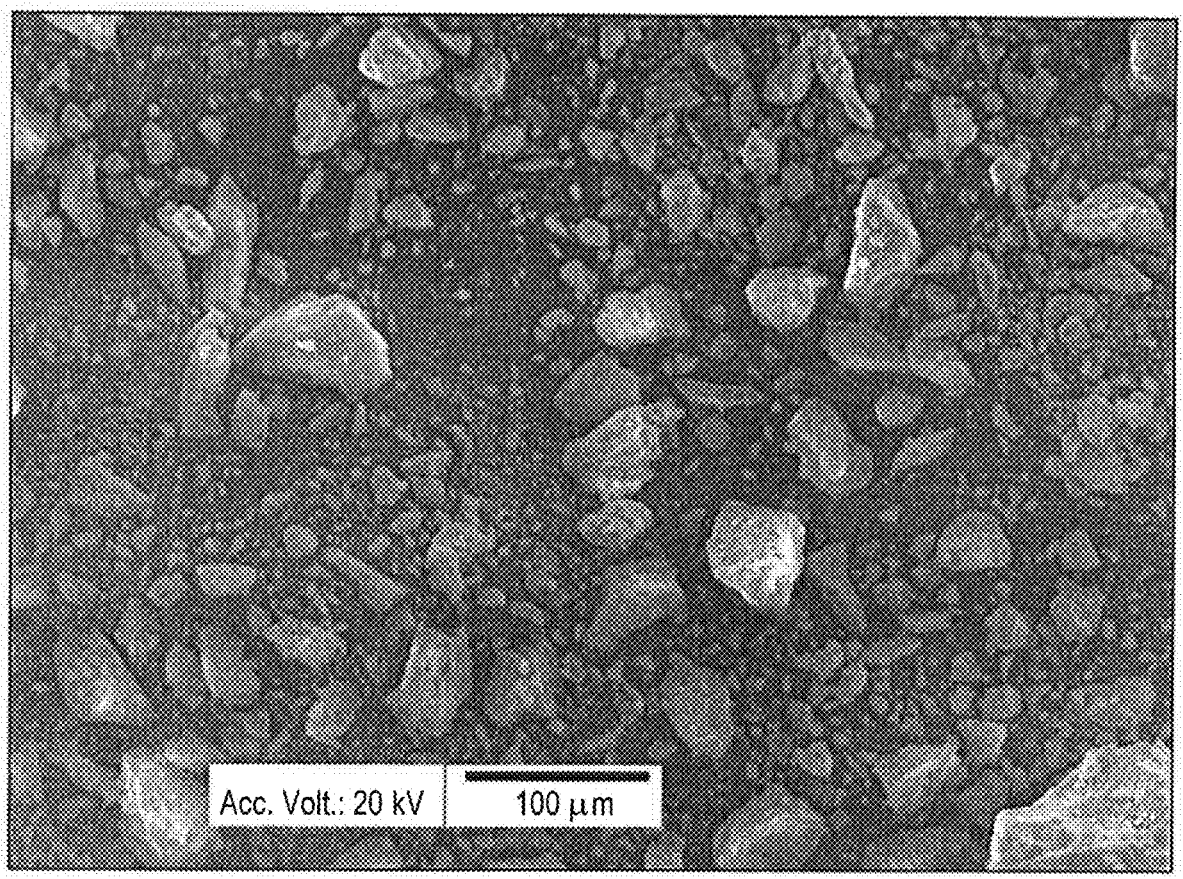
FIG. 4 depicts a scanning electron micrograph of the calcium hydroxide nanoparticles synthesized with carob pulp extract.

Scanning electron microscopy was used to confirm the structural findings of TEM. Scanning electron micrographs of the Ca(OH)$_2$NPs confirmed that the nanoparticles have hexagonal shapes and sizes in the nano range (FIG. 4).

Figure 5:
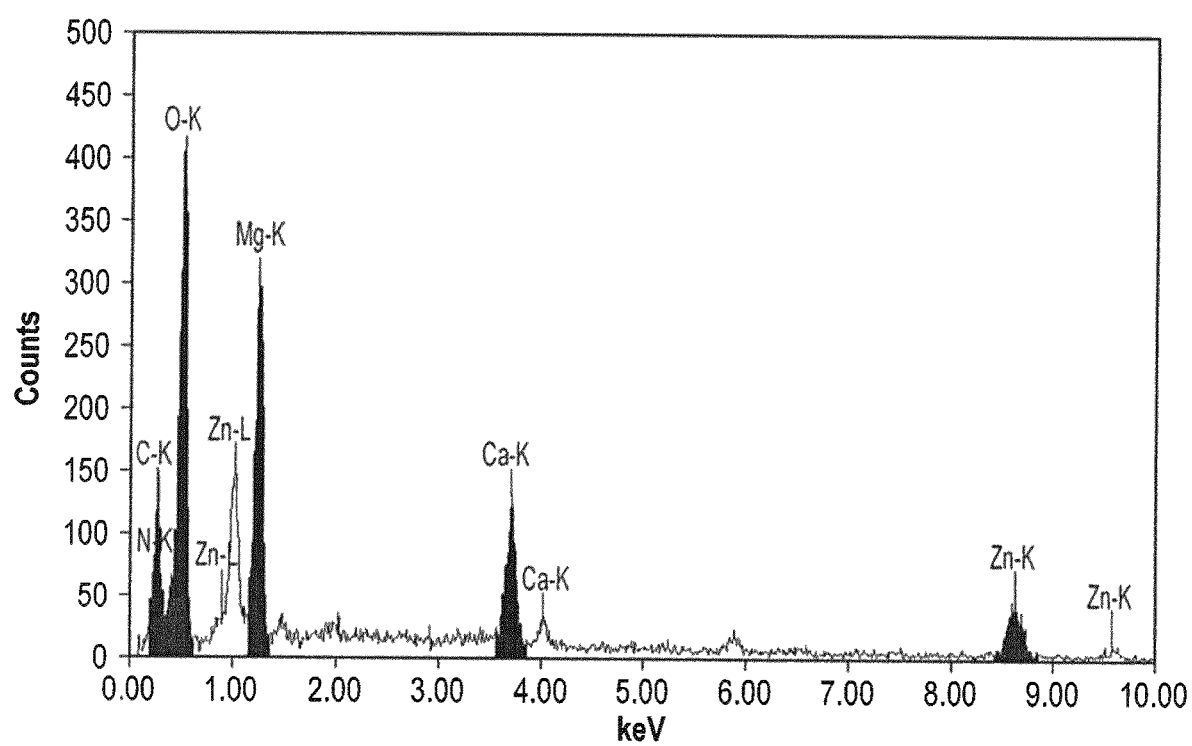
FIG. 5 depicts an energy dispersive X-ray spectrum of the calcium hydroxide nanoparticles synthesized with carob pulp extract.

Energy dispersive X-ray analysis (EDS) was used to determine the inorganic and organic components of the Ca(OH)$_2$NPs. The EDS spectrum demonstrates that the Ca(OH)$_2$NPs have oxygen, nitrogen, zinc, magnesium, and calcium (FIG. 5).

It is to be understood that the calcium hydroxide nanoparticles synthesized with carob pulp extract are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing calcium hydroxide nanoparticles with carob pulp extract, comprising:
    (a) heating ethylene glycol, wherein heating the ethylene glycol is performed in an ultrasonic water bath heated to a temperature of about 99.9° C.;
    (b) adding calcium hydroxide to the ethylene glycol to form a first mixture;
    (c) heating the first mixture, wherein heating the first mixture is performed in an ultrasonic water bath heated to a temperature of about 99.9° C.;
    (d) adding a carob pulp aqueous extract to the first mixture to form a second mixture;
    (e) heating the second mixture wherein heating the second mixture is performed in an ultrasonic water bath heated to a temperature of about 99.9° C.;
    (f) adding sodium hydroxide to the second mixture to form a third mixture;
    (g) heating the third mixture wherein heating the third mixture is performed in an ultrasonic water bath heated to a temperature of about 99.9° C.;
    (h) resting the third mixture after heating;
    (i) centrifuging the third mixture and collecting a colloid sediment, wherein the centrifuging is at 1500 rpm for 30 minutes and repeated a plurality of times;
    (j) extracting chemical contaminants from the colloid sediment to provide a purified colloid sediment; and
    (k) drying the purified colloid sediment to obtain the Ca(OH)$_2$ nanoparticles, wherein the nanoparticles have a minimum diameter of 31.22 nm and a maximum diameter of 81.22 nm.

2. The method of synthesizing calcium hydroxide nanoparticles with carob pulp extract of claim 1, further comprising synthesizing the carob fruit aqueous extract by:
    collecting carob fruit grown in Saudi Arabia;
    drying the carob fruit to produce dried carob fruit;
    grinding the dried carob fruit to produce powdered carob fruit; and
    suspending the powdered carob fruit in a liquid to produce carob fruit aqueous extract.

3. The method of synthesizing calcium hydroxide nanoparticles with carob pulp extract of claim 2, wherein the liquid is water.

4. The method of synthesizing calcium hydroxide nanoparticles with carob pulp extract of claim 1, wherein about 50 ml of the ethylene glycol is heated in the ultrasonic water bath for about 10 minutes.

5. The method of synthesizing calcium hydroxide nanoparticles with carob pulp extract of claim 4, wherein about 25 g of the calcium hydroxide is added to the ethylene glycol and stirred until the calcium hydroxide is completely dissolved.

6. The method of synthesizing calcium hydroxide nanoparticles with carob pulp extract of claim 5, wherein about 50 ml of the carob pulp aqueous extract is added to the first mixture over a period of about 15 minutes.

7. The method of synthesizing calcium hydroxide nanoparticles with carob pulp extract of claim 6, wherein about a 1 M concentration of the NaOH is added to the second mixture over a period of about 5 minutes.

8. The method of synthesizing calcium hydroxide nanoparticles with carob pulp extract of claim 5, wherein the resting occurs at room temperature.

9. The method of synthesizing calcium hydroxide nanoparticles with carob pulp extract of claim 5, wherein contaminants are extracted from the colloid sediment by adding isopropanol to the colloid sediment, mixing the isopropanol and the colloid sediment, centrifuging the isopropanol and the colloid sediment, discarding the supernatant and collecting the colloid sediment after centrifuging the isopropanol and the colloid sediment.

* * * * *

UNITED STATES PATENT AND TRADEMARK OFFICE
CERTIFICATE OF CORRECTION

| | |
|---|---|
| PATENT NO. | : 10,780,111 B1 |
| APPLICATION NO. | : 16/397286 |
| DATED | : September 22, 2020 |
| INVENTOR(S) | : Alsalhi et al. |

It is certified that error appears in the above-identified patent and that said Letters Patent is hereby corrected as shown below:

On the Title Page

Item (72) Inventors: Sandhansamy Devanesan, Riyadh (SA) should be: Sandhanasamy Devanesan, Riyadh (SA)

Signed and Sealed this
Seventh Day of February, 2023

*Katherine Kelly Vidal*

Katherine Kelly Vidal
*Director of the United States Patent and Trademark Office*